US00PP36019P2

(12) United States Plant Patent
Hofmann

(10) Patent No.: US PP36,019 P2
(45) Date of Patent: Jul. 16, 2024

(54) ***NEMESIA* PLANT NAMED 'INNEMCONUT'**

(50) Latin Name: *Nemesia hybrida*
Varietal Denomination: 'INNEMCONUT'

(71) Applicant: Silvia Hofmann, Mainz (DE)

(72) Inventor: Silvia Hofmann, Mainz (DE)

(73) Assignee: INNOVAPLANT ZIERPFLAZEN GmbH+Co. KG, Gensingen (DE)

( * ) Notice: Subject to any disclaimer, the term of this patent is extended or adjusted under 35 U.S.C. 154(b) by 0 days.

(21) Appl. No.: 18/367,962

(22) Filed: Sep. 13, 2023

(51) Int. Cl.
*A01H 5/02* (2018.01)
*A01H 6/00* (2018.01)

(52) U.S. Cl.
USPC ..... Plt./458

(58) Field of Classification Search
USPC ..... Plt./458
See application file for complete search history.

*Primary Examiner* — Susan McCormick Ewoldt
(74) *Attorney, Agent, or Firm* — C. Anne Whealy

(57) ABSTRACT

A new and distinct cultivar of *Nemesia* plant named 'INNEMCONUT', characterized by its compact and upright to somewhat outwardly spreading plant habit; moderately vigorous growth habit; freely branching habit; freely flowering habit; long flowering period; fragrant white-colored flowers; and good container and garden performance.

2 Drawing Sheets

Figure 1:
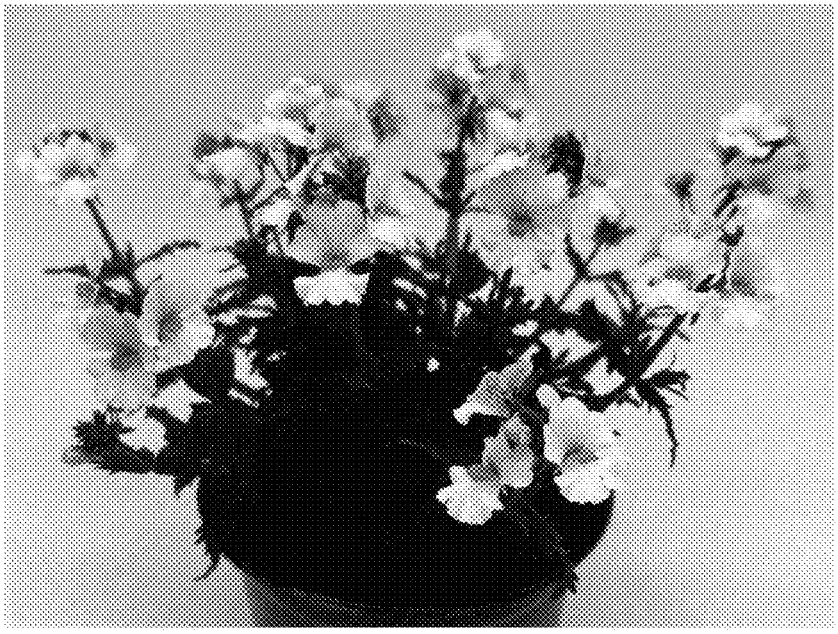

Botanical designation: *Nemesia hybrida.*
Cultivar denomination: 'INNEMCONUT'.

BACKGROUND OF THE INVENTION

The present invention relates to a new and distinct cultivar of *Nemesia* plant, botanically known as *Nemesia hybrida*, and hereinafter referred to by the name 'INNEMCONUT'.

The new *Nemesia* plant is a product of a planned breeding program conducted by the Inventor in Heidesheim, Germany. The objective of the breeding program is to create compact and freely branching *Nemesia* plants with good summer garden performance and numerous attractive and fragrant flowers.

The new *Nemesia* plant originated from a cross-pollination made by the Inventor during the summer of 2018 in Heidesheim, Germany of a proprietary selection of *Nemesia hybrida* identified as code number N 02 82-1, not patented, as the female, or seed, parent with a proprietary selection of *Nemesia hybrida* identified as code number N 17 12-150, not patented, as the male, or pollen, parent. The new *Nemesia* plant was discovered and selected by the Inventor as a single flowering plant from within the progeny of the stated cross-pollination in a controlled environment in Heidesheim, Germany during the spring of 2019.

Asexual reproduction of the new *Nemesia* plant by terminal vegetative cuttings in a controlled environment in Heidesheim, Germany since the spring of 2019, has shown that the unique features of this new *Nemesia* plant are stable and reproduced true to type in successive generations.

SUMMARY OF THE INVENTION

Plants of the new *Nemesia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INNEMCONUT'. These characteristics in combination distinguish 'INNEMCONUT' as a new and distinct *Nemesia* plant:

1. Compact and upright to somewhat outwardly spreading plant habit.
2. Moderately vigorous growth habit.
3. Freely branching habit.
4. Freely flowering habit.
5. Long flowering period.
6. Fragrant white-colored flowers.
7. Good container and garden performance.

Plants of the new *Nemesia* differ primarily from plants of the female parent selection in the following characteristics:

1. Plants of the new *Nemesia* are more freely branching than plants of the female parent selection.
2. Flowers of plants of the new *Nemesia* are sterile whereas flowers of plants of the female parent selection are fertile.

Plants of the new *Nemesia* differ primarily from plants of the male parent selection in the following characteristics:

1. Flowers of plants of the new *Nemesia* are white in color whereas flowers of plants of the male parent selection are light red in color.
2. Flowers of plants of the new *Nemesia* are sterile whereas flowers of plants of the male parent selection are fertile.

Plants of the new *Nemesia* can be compared to plants of *Nemesia hybrida* 'Intraiwhi', disclosed in U.S. Plant Pat. No. 17,502. In side-by-side comparisons, plants of the new *Nemesia* differ primarily from plants of 'Intraiwhi' in the following characteristics:

1. Plants of the new *Nemesia* are more compact than plants of 'Intraiwhi'.
2. Plants of the new *Nemesia* are more freely branching than plants of 'Intraiwhi'.

3. Flowers of plants of the new *Nemesia* are larger than flowers of plants of 'Intraiwhi'.

BRIEF DESCRIPTION OF THE PHOTOGRAPHS

The accompanying colored photographs illustrate the overall appearance of the new *Nemesia* plant showing the colors as true as it is reasonably possible to obtain in colored reproductions of this type. Colors in the photographs may differ slightly from the color values cited in the detailed botanical description which accurately describe the colors of the new *Nemesia* plant.

The photograph on the first sheet (FIG. 1) is a side perspective view of a typical flowering plant of 'INNEMCONUT' grown in a container.

Figure 2:
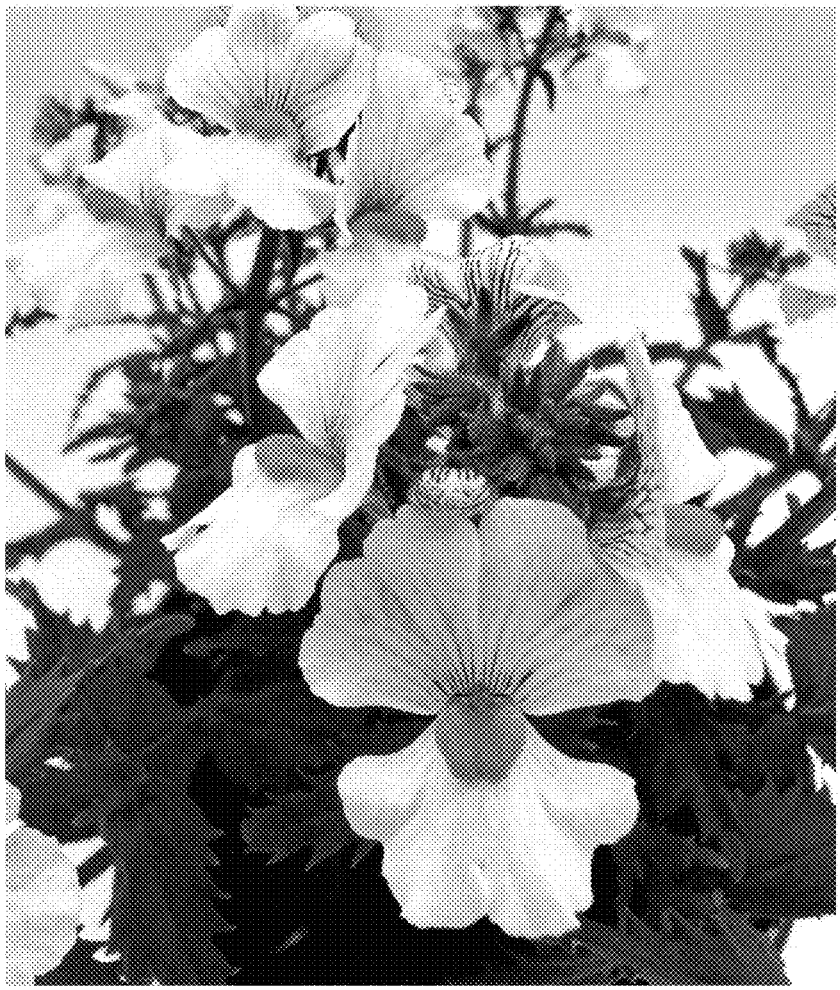

The photograph on the second sheet (FIG. 2) is a close-up view of a typical flowering plant of 'INNEMCONUT'.

DETAILED BOTANICAL DESCRIPTION

The aforementioned photographs and following observations and measurements describe plants grown during the late spring in 813-ml containers in a glass-covered greenhouse in Loudon, New Hampshire and under cultural practices typical of commercial *Nemesia* production. During the production of the plants, day and night temperatures averaged 20 C. Plants were eight weeks from planting rooted cuttings when the photographs and description were taken. In the following description, color references are made to The Royal Horticultural Society Colour Chart, 2015 Edition, except where general terms of ordinary dictionary significance are used.

Botanical classification: *Nemesia hybrida* 'INNEMCONUT'.

Parentage:

*Female, or seed, parent*.—Proprietary selection of *Nemesia hybrida* identified as code number N 05 82-1, not patented.

*Male, or pollen, parent*.—Proprietary selection of *Nemesia hybrida* identified as code number N 17 12-150, not patented.

Propagation:

*Type*.—By terminal vegetative cuttings.

*Time to initiate roots, summer*.—About ten days at substrate temperatures about 20 C.

*Time to initiate roots, winter*.—About twelve days at substrate temperatures about 20 C.

*Time to produce a rooted young plant, summer*.—About 14 days.

*Time to produce a rooted young plant, winter*.—About 16 days.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; dense.

Plant description:

*Plant and growth habit*.—Herbaceous annual; compact and upright to somewhat outwardly spreading plant habit; moderately vigorous growth habit; moderate growth rate; freely branching habit with about 14 to 16 primary branches with secondary laterals developing potentially at every node.

*Plant height*.—About 17 cm.

*Plant diameter*.—About 31 cm.

Lateral branch description:

*Length*.—About 18 cm.

*Diameter*.—About 3 mm.

*Internode length*.—About 2.5 cm to 3 cm.

*Strength*.—Moderately strong; flexible.

*Aspect*.—Mostly upright to somewhat outwardly and curving upright.

*Texture and luster*.—Longitudinally ridged; smooth, glabrous; somewhat glossy.

*Color, developing*.—Close to 144A.

*Color, developed*.—Close to 146A.

Leaf description:

*Arrangement*.—Opposite, simple; sessile.

*Length*.—About 5 cm.

*Width*.—About 2.3 cm to 2.5 cm.

*Shape*.—Ovate to narrowly ovate.

*Apex*.—Acute.

*Base*.—Obtuse.

*Margin*.—Dentate.

*Texture and luster, upper and lower surfaces*.—Smooth, glabrous; slightly glossy.

*Venation pattern*.—Pinnate; arcuate.

*Color*.—Developing and fully expanded leaves, upper surface: Close to 137A; venation, close to between 144A and 146A. Developing and fully expanded leaves, lower surface: Close to 147B; venation, close to 144A.

Flower description:

*Flower arrangement and habit*.—Bilabiate single flowers arranged in terminal and axillary racemes; flowers develop acropetally towards the apex; flowers face mostly outwardly; freely flowering habit with about 18 to 26 flowers per inflorescence and numerous flowers developing per plant during the flowering season.

*Fragrance*.—Moderate; floral, pleasant.

*Natural flowering season*.—Long flowering period, in New Hampshire, plants flower from spring until autumn; flowering continuous during this period; plants begin flowering about four weeks after planting rooted young plants.

*Flower longevity*.—Depending on temperature, flowers last about one to two weeks on the plant; petals not persistent, sepals and reproductive organs persistent.

*Inflorescence length*.—About 7.2 cm.

*Inflorescence diameter*.—About 3.2 cm.

*Flower size*.—About 1.6 cm by 1.7 cm.

*Flower depth*.—About 1.1 cm.

*Flower buds*.—Length: About 4 mm. Diameter: About 2.25 mm. Shape: Oval. Texture and luster: Smooth, glabrous; somewhat glossy. Color, developing sepals: Close to 146A.

*Petals*.—Arrangement: Five petals; two upper and two lateral petals fused at base to form an upright lobed and arched upper or banner lip; lower petal modified into a large recurved lower lip with convex bi-lobed protuberance and short nectar spur. Spur length: About 7 mm. Spur diameter, distally: About 1 mm. Spur texture and luster: Smooth, glabrous; matte. Spur color: Close to 157B. Lobe length: Upper petals: About 9 mm. Lateral petals: About 8 mm. Lower petal: About 8 mm to 9 mm. Lobe width: Upper petals: About 5 mm. Lateral petals: About 6 mm. Lower petal: About 7 mm. Shape: Upper and lateral petals: Oblong to obovate. Lower petal:

Broadly spatulate. Apex, upper petals: Obtuse. Apex, lateral petals: Obtuse; occasionally retuse. Apex, lower petal: Broadly obtuse. Margin, upper and lateral petals: Entire; not undulate. Margin, lower petal: Entire, recurved and ruffled. Texture and luster, all petals, upper and lower surfaces: Smooth, glabrous; matte. Color, upper and lateral petals: When opening and fully opened, upper surface: Close to 157A to 157B; venation, close to 157A to 157B; fine stripes, close to 79A; color does not change with subsequent development. When opening and fully opened, lower surface: Close to NN155C to NN155D; venation, close to NN155C to NN155D; color does not change with subsequent development. Color, lower petal: When opening and fully opened, upper surface: Close to 157A to 157B; venation, close to 157A to 157B; protuberance, close to 17A; color does not change with subsequent development. When opening and fully opened, lower surface: Close to NN155C to NN155D; venation, close to NN155C to NN155D; color does not change with subsequent development. Color, throat: Close to 157A and 17A. Color, tube: Close to NN155C to NN155D.

*Sepals*.—Arrangement: Calyx star-shaped with five sepals fused at the base. Calyx length: About 4 mm. Calyx diameter: About 3 mm. Length: About 4 mm. Width: About 1 mm. Shape: Elliptic. Apex: Acute. Margin: Entire. Texture and luster, upper and lower surfaces: Slightly pubescent; matte to slightly glossy. Color, upper and lower surfaces: Close to between 146A and 147A.

*Peduncles*.—Length: About 7.2 cm. Diameter: About 3 mm. Angle: Mostly upright to somewhat curving upwardly. Strength: Moderately strong; flexible. Texture and luster: Smooth, glabrous; slightly glossy. Color: Close to between 146A and 147A.

*Pedicels*.—Length: About 1.2 cm. Diameter: About 1 mm. Angle: About 30 to 45 degrees from peduncle axis. Strength: Moderately strong; flexible. Texture and luster: Smooth, glabrous; slightly glossy. Color: Close to 146A.

*Reproductive organs*.—Stamens: Quantity: Two to four per flower. Filament length: About 9 mm. Filament color: Close to NN155D. Anther length: Less than 1 mm. Anther shape: Oblong. Anther color: Close to 12A. Pollen amount: None observed. Pistils: To date, pistil development has not been observed on plants of the new *Nemesia*.

*Seeds and fruits*.—To date, seed and fruit development have not been observed on plants of the new *Nemesia*.

Pathogen & pest resistance: To date, plants of the new *Nemesia* have not been observed to be resistant to pathogens and pests common to *Nemesia* plants.

Garden performance: Plants of the new *Nemesia* have been observed to have good summer garden performance and to tolerate wind and rain and temperatures ranging from about 5 C to about 35 C.

It is claimed:

1. A new and distinct *Nemesia* plant named 'INNEMCONUT' as illustrated and described.

* * * * *